US009668778B2

(12) United States Patent
Droulout

(10) Patent No.: US 9,668,778 B2
(45) Date of Patent: Jun. 6, 2017

(54) INSTRUMENT SYSTEM FOR CARRYING OUT A SURGICAL PROCEDURE ON THE VERTEBRAE COMPRISING TEMPORARY IMMOBILIZATION MEANS

(71) Applicant: SAFE ORTHOPAEDICS, Eragny sur Oise (FR)

(72) Inventor: Thomas Droulout, Poissy (FR)

(73) Assignee: SAFE ORTHOPAEDICS, Eragny sur Oise (FR)

( * ) Notice: Subject to any disclaimer, the term of this patent is extended or adjusted under 35 U.S.C. 154(b) by 127 days.

(21) Appl. No.: 14/402,449

(22) PCT Filed: May 28, 2013

(86) PCT No.: PCT/FR2013/051183
§ 371 (c)(1),
(2) Date: Mar. 9, 2015

(87) PCT Pub. No.: WO2013/178933
PCT Pub. Date: Dec. 5, 2013

(65) Prior Publication Data
US 2015/0173803 A1    Jun. 25, 2015

(30) Foreign Application Priority Data

May 28, 2012  (FR) ...................................... 12 54896

(51) Int. Cl.
*A61B 17/70*       (2006.01)
(52) U.S. Cl.
CPC ........ *A61B 17/7037* (2013.01); *A61B 17/708* (2013.01); *A61B 17/7085* (2013.01); *A61B 17/7091* (2013.01)

(58) Field of Classification Search
CPC ............ A61B 17/7037; A61B 17/7091; A61B 17/7085; A61B 17/708; A61B 17/1604; A61B 17/1655; A61B 17/1757; A61B 17/320016; A61B 17/3417; A61B 17/3421; A61B 17/7005; A61B 17/701; A61B 17/7011; A61B 17/7032; A61B 17/7038; A61B 17/704; A61B 17/7082; A61B 17/346; A61B 17/7002
(Continued)

(56) References Cited

U.S. PATENT DOCUMENTS 3,509,873 A    5/1970 Karlin et al.
7,179,261 B2 * 2/2007 Sicvol ................ A61B 17/7091
                                                  606/86 A
(Continued)

FOREIGN PATENT DOCUMENTS

EP    0455282 A2   11/1991
FR    2874496 A1   3/2006
(Continued)

*Primary Examiner* — Pedro Philogene
(74) *Attorney, Agent, or Firm* — Bachman & LaPointe, P.C.

(57) ABSTRACT

An instrument system for carrying out a surgical procedure on vertebrae by a posterior or posterolateral approach, made up of at least one tube and at least one spinal screw capable of engaging with the proximal end of said tube and having a head with multi-axial mobility, characterized by also comprising a wedge for temporarily blocking the position of the screw head.

10 Claims, 4 Drawing Sheets

(58) Field of Classification Search
USPC ......... 606/246–479, 86 A, 104, 914, 916, 99
See application file for complete search history.

(56) References Cited

U.S. PATENT DOCUMENTS

| | | | | |
|---|---|---|---|---|
| 2005/0149053 | A1* | 7/2005 | Varieur | A61B 17/7091 |
| | | | | 606/104 |
| 2006/0011712 | A1 | 1/2006 | Oggioni | |
| 2006/0111712 | A1* | 5/2006 | Jackson | A61B 17/7037 |
| | | | | 606/914 |
| 2008/0262318 | A1* | 10/2008 | Gorek | A61B 17/0206 |
| | | | | 600/235 |
| 2009/0149887 | A1* | 6/2009 | Schlaepfer | A61B 17/7034 |
| | | | | 606/278 |

FOREIGN PATENT DOCUMENTS

| | | |
|---|---|---|
| FR | 2954689 A1 | 7/2011 |
| WO | 2011080426 A2 | 7/2011 |

\* cited by examiner

INSTRUMENT SYSTEM FOR CARRYING OUT A SURGICAL PROCEDURE ON THE VERTEBRAE COMPRISING TEMPORARY IMMOBILIZATION MEANS

BACKGROUND

The present invention relates to the field of surgical instruments for spinal stabilisation operations using bone-anchor elements such as screws by a posterior or postero-lateral approach.

The invention relates specifically to an instrument kit according to the invention intended mainly, but not exclusively, for lumbar, thoracic or even posterior cervical spinal osteosynthesis surgery, by minimally invasive or open surgical approaches.

In the event of anatomical malfunctions of the spinal column, bone anchors such as pedicular or vertebral screws are placed in the vertebra, connected to one another by connection elements such as rods or plates.

Prior Art

Application PCT/FR10/000880, by the applicant, is known from the prior art. Said document discloses instrumentation for fixing at least two spinal vertebrae by bone-anchor implants such as pedicular screws including a bone-anchor element intended for being fixed to a vertebra, pre-mounted on a disposable mounting tube, and a sealed sterile packaging container.

Said prior art document also relates to a kit of instruments for installing or removing a spinal implant comprising at least two threaded bone-anchor elements, a connecting member such as a rod or a plate mechanically connecting the bone-anchor elements and locking elements for locking the connecting member in position relative to the anchor elements, in order to perform all the surgical deeds linked to the installation or removal of said implant, characterised in that all of said necessary instruments are disposable and packaged under sterile conditions in one or more sealed containers.

French patent FR2874496 is also known, describing a retractor for the tissues of a patient, of the type including two blades having a proximal end and a distal end, respectively, said blades being arranged such as to form a surgical channel open at the proximal and distal ends of said blades, characterised in that the retractor comprises at least one matching blade to form a retractor with at least three blades, said blades separating from one another by pivoting of the distal ends thereof such as to form a tapering widened surgical channel.

European patent application EP0455282 is also known, describing an autostatic separator including a polygonal winder frame connected to a plurality of dilators.

When inserted deeply into the body of the patient, it keeps the edges of the incision open. The sides are hingedly connected to one another and to two opposing hinges.

Another example of a separator is described in U.S. Pat. No. 3,509,873.

Drawbacks of the Prior Art

Said prior art retractor solutions have two major drawbacks. First of all, these solutions lead to two separate devices:
one or more tubes making it possible to support the spinal screw and, during the intervention, to guide the linking rod which is inserted in the screw head, and then to insert and screw a plug locking the rod in the screw head;
a second device made up of a plurality of blades capable of holding the tissues in the area around the operating area.

In the prior art solutions, said known devices take up a considerable amount of space in the surgical area, which makes it necessary either to widen the incision, or to make do with a narrow field of vision and work. In both these cases, the surgeon is impeded in the execution of the operation and the surgical deed.

The second drawback is that the second device must be positioned prior to inserting the screws. Once it is placed in the operating area, the device limits the possible angulation of the tubes and thus complicates spinal screwing and the insertion of the proximal end of the tube on the spinal screw when the screw is not pre-mounted on the tube.

Finally, in all the prior art solutions, the retractor (second device) is a complex surgical instrument, requiring thorough, complicated sterilisation, given the complex shapes and the presence of multiple hinged sections, after each use. Said complex additional device furthermore creates an additional cost which is difficult to afford given the economic constraints of the healthcare industry.

SUMMARY

In order to solve the drawbacks of the prior art, the present invention proposes a solution that consists of completing the spinal tube(s) by a simple accessory at least making it possible to use the tube not only for the initial function thereof of installing the spinal screw, inserting the linking rod and tightening the plug, but also to grant the tube(s) an additional function of retracting the tissues.

For this purpose, the invention, in the broadest sense thereof, relates to an instrument system for carrying out a surgical procedure on vertebrae by a posterior or postero-lateral approach, made up of at least one tube and at least one spinal screw capable of engaging with the proximal end of said tube and having a head with multiaxial mobility, characterised by also comprising a wedge for temporarily blocking the position of the screw head.

The expression "distal end" is understood to refer to the end furthest from the implant, and the expression "proximal end" is understood to refer to the end closest to the implant.

By making it possible to block the head in any angular position relative to the threaded shank of the screw, the blocking wedge thus makes it possible to keep the tube engaging with the screw in a desired position. The angulation of the tubes is thus improved with respect to the instrument systems of the prior art.

It is understood that blocking the position of the screw head, and thus that of the tube is temporary in the sense that the blocking wedge must be removed in order to place a linking rod on the screw head. The blocking wedge is thus only used temporarily to block the multiaxial movement of the screw head and thus to make it possible to perform certain operations prior to placing the linking rod that require the tubes to be kept in a given position.

Preferably, said wedge has a semi-cylindrical end, with a shape that matches that of the U-shaped notch for receiving a linking rod, provided on the screw head.

According to a first alternative embodiment, said blocking wedge is made up of the proximal end of an insert sliding inside said tube.

According to a second alternative embodiment, said blocking wedge has a means for connecting with an insert sliding inside said tube.

Advantageously, the blocking wedge is capable of being inserted into the tube, from the distal end thereof.

Advantageously, said insert has at least one guiding rib with a cross-section that matches that of at least one guiding groove provided in the cavity formed in said tube.

According to a specific embodiment, said tubes are made up of two half shells capable of engaging with the head of a spinal screw such as to allow proximal tilting of at least one of said half shells relative to the head of said spinal screw. Given this configuration, the function of guiding the first type of prior art device and the function of retracting the tissues of the second type of prior art device (retractor) are performed by the same single instrument, namely the tube.

According to a first alternative embodiment, said blocking wedge has a means of reversible attachment to said insert.

According to a second alternative embodiment, said means of reversible attachment is made up of a snap-fitting area.

Advantageously, said means of reversible attachment is made up of a screwing area.

According to an advantageous embodiment, said insert has an area for locking to said tube by screwing. Said insert is advantageously made up of the insert for placing the plug for locking the screw head.

The invention also relates to a wedge for temporary blocking of the position of the screw head, capable of being inserted into the tube, from the distal end thereof, having a semi-cylindrical end with a shape that matches that of the U-shaped notch for receiving a linking rod, provided on the screw head.

BRIEF DESCRIPTION OF THE DRAWINGS

Further objectives and advantages of the invention will become apparent from the following description made in reference to the appended drawings, wherein.

DETAILED DESCRIPTION

Figure 1:
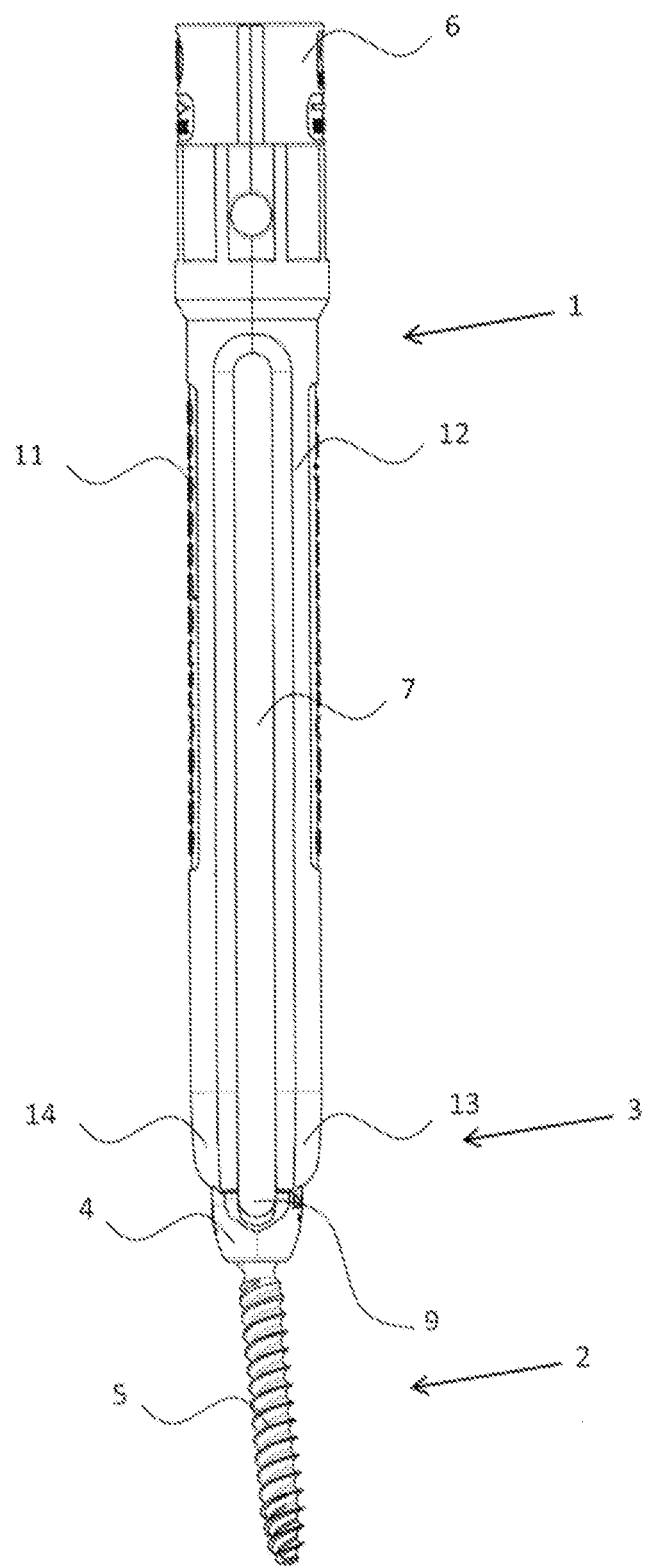
FIG. 1 is a perspective view of two tubes during the placement of screws in a vertebra
Figure 2:
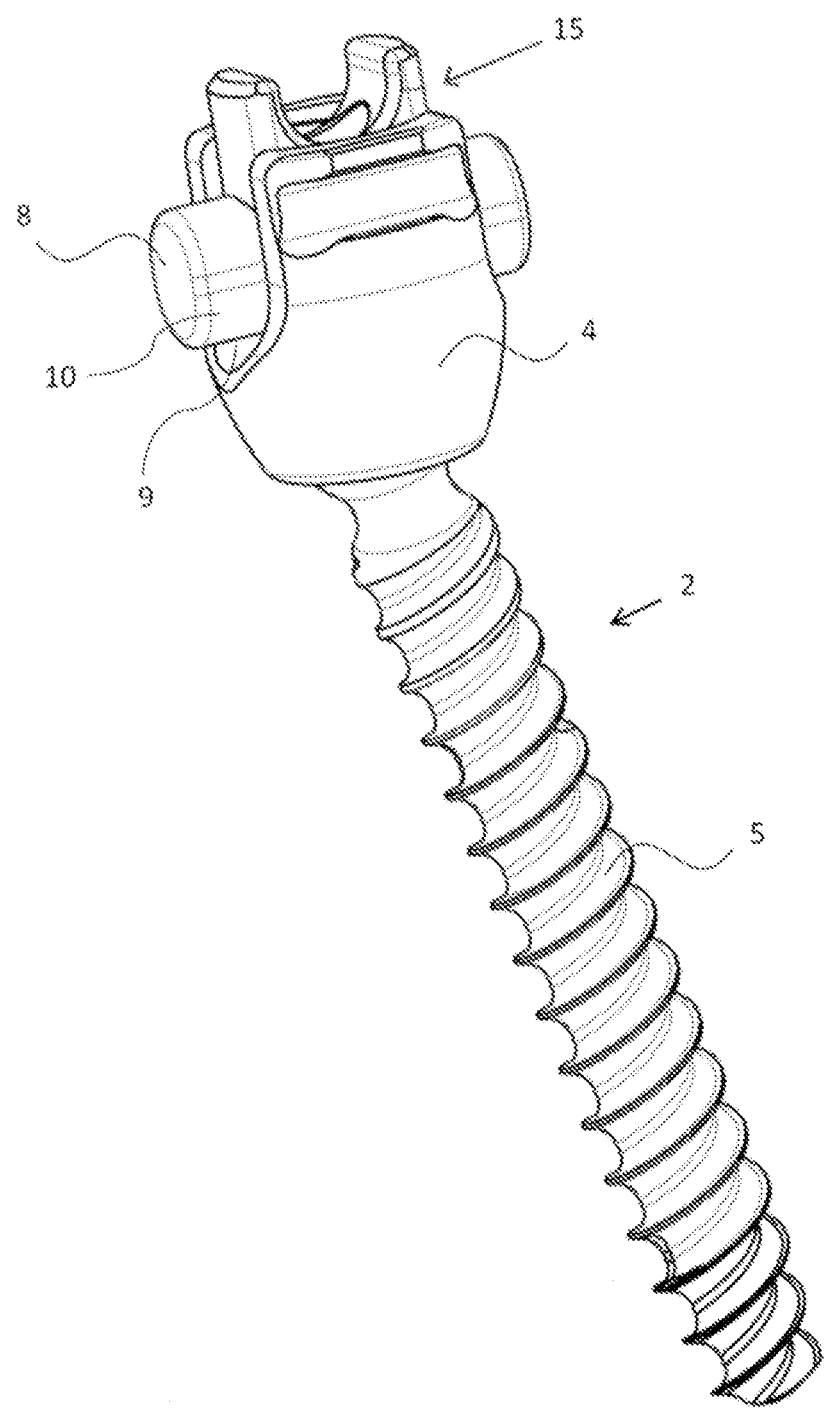
FIG. 2 is a view of a wedge according to the invention combined with a pedicular screw

FIG. 1 is a profile view of a tube (1) for spinal fixing during the placement of a screw (2) in a vertebra, with tubes known from the prior art.

The tube (1) supports at the proximal end (3) thereof a spinal (or "pedicular") screw (2) which is advantageously pre-mounted. The connection between the proximal end (3) and the screw (2) is provided by means of a head (4) having a fastening groove engaging with a shoulder provided on the inner surface of the proximal end (3) of the tube (1).

The screw head (4) and the threaded portion (5) engage by means of a ball-and-socket joint enabling multiaxial positioning and locking by means of the linking rod and a threaded plug which rests, optionally by means of a matching part, the linking rod against the upper end of the threaded rod (5) when the assembly is in place and correctly positioned.

The pedicular screw (2) is intended for being fixed to vertebrae. Said screw includes a bone-anchor means (5) extended by a slotted head (4) for receiving an intervertebral linking rod, not shown. When the rod is in place, a screwable plug (not shown) is screwed into the head (4) via a thread, in order to lock the assembly.

The material most commonly used to manufacture the screws is titanium. In a specific configuration of the invention, the material used for manufacturing can be any implantable material, currently known or otherwise, such as PEEK, stainless steel, cobalt chromium, or even a fibreglass or carbon-fibre composite. Coatings such as HATCP (HydroxyApatite TriCalcium Phosphate) or others can also be applied to improve the bone anchoring or overall mechanical resistance of the implant.

The installation of the screw (2) and the placement of the rod, followed by the locking thereof with the screwable plug are provided by an instrument described in prior art patent PCT/FR10/000880, the contents of which is included in the present application and incorporated by reference to this application.

The tube (1) is, in the described example, made up of two half shells (11, 12), respectively, hingedly connected by the proximal ends thereof (13, 14), such as to allow tilting relative to the screw head (4), when the two half shells are released.

A ring (6) provides the locking of the two half shells (11, 12) such as to form a tube (1) which is closed during certain phases of use.

The tube (1) has longitudinal openings (7) allowing the insertion of a linking rod and the movement thereof into the U-shaped slot provided in the screw head (4).

It should be noted that the invention is not limited to the implementation of tubes formed by two half shells, and can also be applied to integral tubes.

However, the embodiment in the form of two assembled half shells is a preferred embodiment.

The invention aims to enable the use of such tubes known in the prior art to additionally provide the retraction of tissues, without needing to use a complementary instrument such as the retractors that are known from the prior art.

For this purpose, the invention includes an accessory part made up of a wedge (15) which is provisionally inserted instead of the linking rod, making it possible temporarily to ensure the blocking of the hinged connection of the head (4) of the screw (2) relative to the threading axis (5).

Said wedge (15) is inserted in the space intended for receiving a linking rod and engages with the top frontal end of the threaded rod (5), optionally by means of a matching part, in order to ensure the locking thereof relative to the screw head (4).

The end (8) of the wedge (15) has a thickness corresponding to the section of the U-shaped recess (9) intended for receiving a linking rod, and a semi-cylindrical frontal bearing edge (10) configured to allow the locking of the threaded portion (5) of the screw relative to the head (4).

Figure 3:
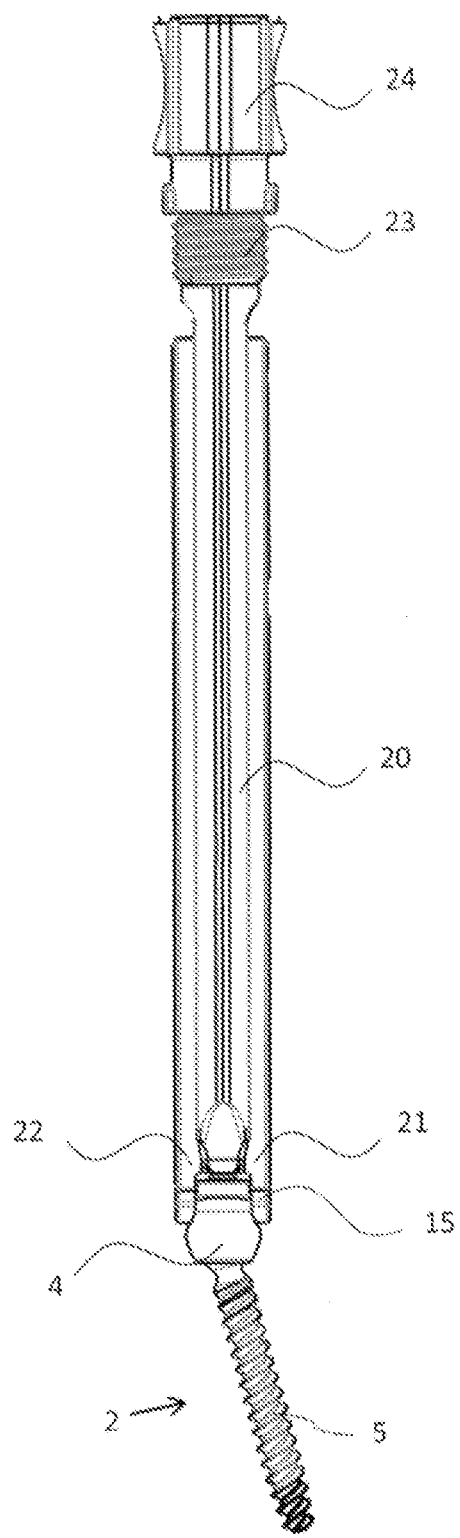
FIG. 3 is a view of a second alternative embodiment of the wedge extended by an insert

The top end of the wedge (15), opposite said bearing edge (10), has a fixing area that matches the proximal end of an insert (20) shown in FIG. 3.

Said insert (20) is advantageously the insert known from the prior art as shown in application PCT/FR10/000880 by the applicant, for pushing the linking rod and inserting the plug screwed into the screw head.

The proximal end (23) of said insert (20) is slotted and has two tabs (21, 22) defining an opening usually intended for the passage of the screwable plug.

The means for fixing the wedge (15) has a shape that matches said proximal end of the insert (20) such as to enable fixing by snap-fitting. The wedge (15) can thus be positioned on the insert, and then inserted by means of said insert (20) sliding longitudinally into the tube until coming into position in the head (4) of the screw (2).

The insert (20) is then locked relative to the tube (1) by screwing via a pivoting thread (23) provided on the distal end of the insert (20). When the insert is screwed onto the tube (1), it exerts a pushing force on the wedge (15), which thus angularly locks the threaded rod (5) relative to the screw head (4), in a position in which the walls of the tube (1) separate the edges of the incision made in the tissues, and thus enable easy access to the surgical operating area.

Figure 4:
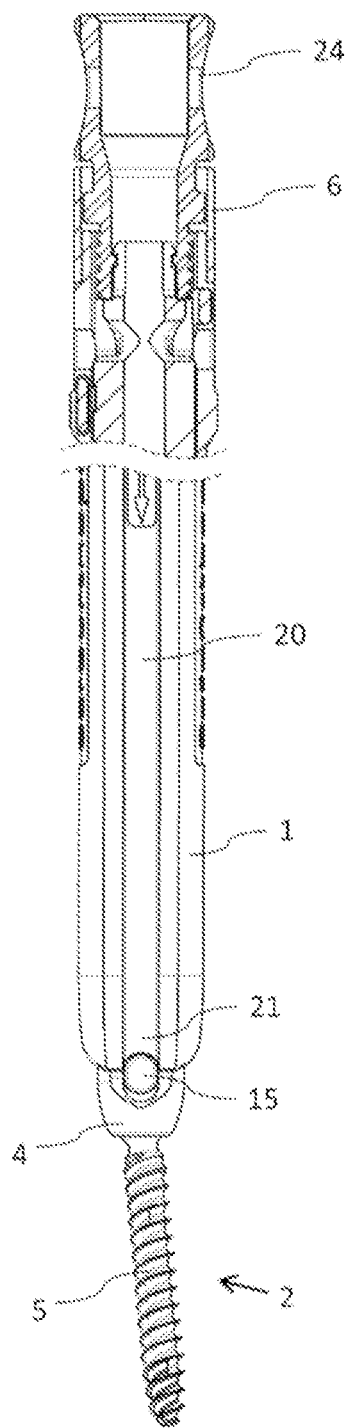
FIG. 4 is a cross-section view of a tube with the insert and the wedge.

FIG. 4 is a longitudinal-section view of the system. The insert (20) has, at the distal end thereof, a pivoting head (24) provided with a thread (23) that can engage with a thread provided on the inside of the tube (1).

According to one alternative, the wedge (15) and the insert can be formed integrally.

According to another alternative, the means for pushing and locking the insert (20) relative to the tube (1) can be made up of an additional part.

The tube (1), the insert (20) and the wedge (15) can be made from injected polymer such as to enable the production of a disposable system.

According to another alternative embodiment, the insert (20) is configured such as to allow the pre-loading of the plug which is placed in the receiving cavity provided at the proximal end of the insert (20), as described in application PCT/FR10/000880 by the applicant. The plug is installed when manufacturing the system, and remains in place, in particular during the use of the system as a tissue retractor, until the step of locking the linking rod.

The use of a plurality of systems during a surgical procedure, each system connected with an spinal screw implanted on consecutive vertebrae, thus makes it possible to expand the tissues in order to form a perfectly accessible working space, with no need to resort to the retractors known from the prior art.

The invention claimed is:

1. An instrument system for carrying out a surgical procedure on vertebrae by a posterior or posterolateral approach, made up of at least one tube and at least one spinal screw capable of engaging with the proximal end of said tube and having a head with multiaxial mobility, comprising a wedge for temporarily blocking the position of the screw head, wherein said wedge has a semi-cylindrical end, with a shape that matches that of the U-shaped notch for receiving a linking rod, provided on the screw head.

2. The instrument system according to claim 1, wherein said blocking wedge is made up of the proximal end of an insert sliding inside said tube.

3. The instrument system according to claim 1, wherein the wedge is capable of being inserted into the tube from the distal end thereof.

4. The instrument system according to claim 1, wherein said blocking wedge has a means for connecting with an insert sliding inside said tube.

5. The instrument system according claim 1, wherein said insert has at least one guiding rib with a cross-section that matches that of at least one guiding groove provided in the cavity formed in said tube.

6. The instrument system according to claim 5, wherein said tube is formed by two half shells capable of engaging with the head of a spinal screw such as to allow proximal tilting of at least one of said half shells relative to the head of said spinal screw.

7. The instrument system according to claim 4, wherein said blocking wedge has a means of reversible attachment on said insert.

8. The instrument system according to claim 7, wherein said means of reversible attachment is made up of a snap-fitting area.

9. The instrument system according to claim 7, wherein said means of reversible attachment is made up of a screwing area.

10. The instrument system according to claim 4, wherein said insert has an area for locking by screwing onto said tube.

* * * * *